United States Patent [19]

Rollenhagen

[11] 4,244,367
[45] Jan. 13, 1981

[54] PROTECTIVE PANTY BRIEF

[76] Inventor: Janet T. Rollenhagen, 3878 Gaines Ct., Simi Valley, Calif. 93063

[21] Appl. No.: 9,283

[22] Filed: Feb. 2, 1979

[51] Int. Cl.³ ............................................. A61F 13/16
[52] U.S. Cl. .................................................. 128/288
[58] Field of Search ................... 128/288, 289, 290 H, 128/291; 2/406

[56] References Cited

U.S. PATENT DOCUMENTS

| | | | |
|---|---|---|---|
| 3,048,176 | 8/1962 | DeWoskin | 128/288 |
| 3,232,293 | 2/1966 | DeWoskin | 128/288 |
| 3,520,304 | 7/1970 | Kubali et al. | 128/288 |
| 3,749,095 | 7/1973 | Toyama | 128/288 |
| 3,816,209 | 6/1974 | DeWoskin et al. | 128/288 |
| 4,023,570 | 5/1977 | Chinai et al. | 128/290 R |

*Primary Examiner*—C. Fred Rosenbaum
*Attorney, Agent, or Firm*—William H. Maxwell

[57] ABSTRACT

A versatile panty for protecting the garments of wearers who suffer from incontinence and do not have complete bladder control and the like, and comprised of stretchable body panels for constriction onto the wearer and including a crotch area coextensively over which there is a protective membrane impervious to liquid restricting said stretch throughout the crotch area, whereby a pad or sanitary napkin or disposable diaper disposed contiguously between the constricting body panels and said crotch area thereof is reliably secure in position, the panty being fully lined in its preferred form and multi-lined throughout the said crotch area.

4 Claims, 8 Drawing Figures

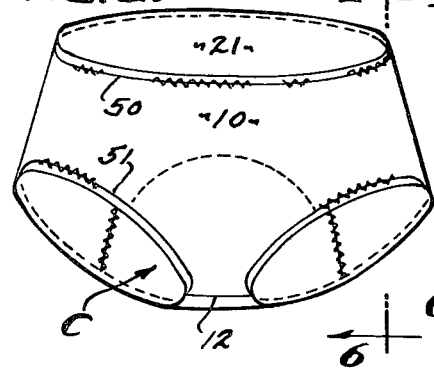
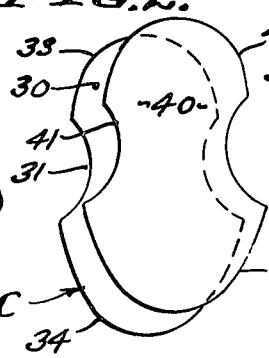
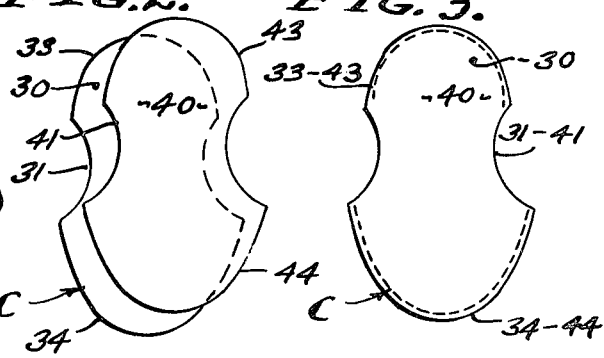
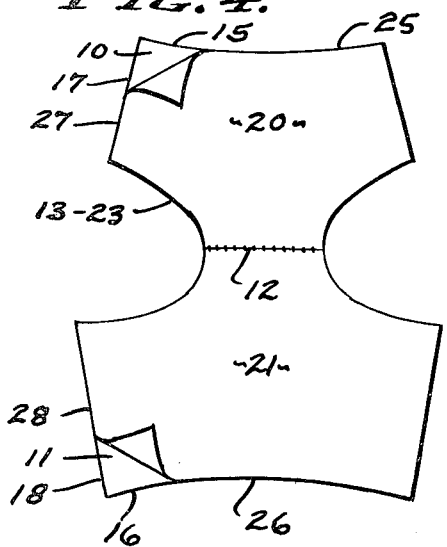
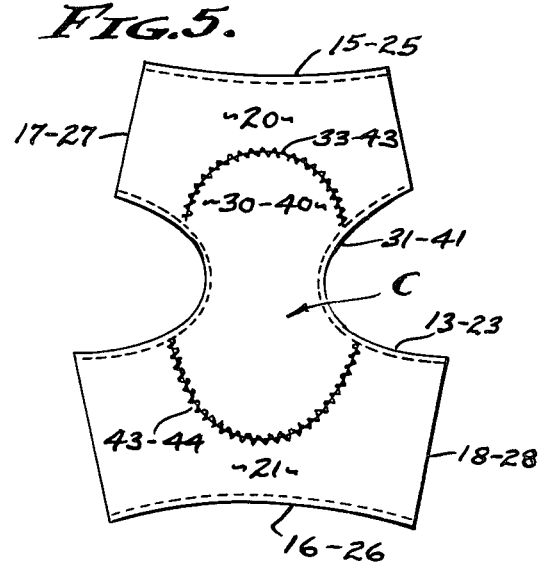
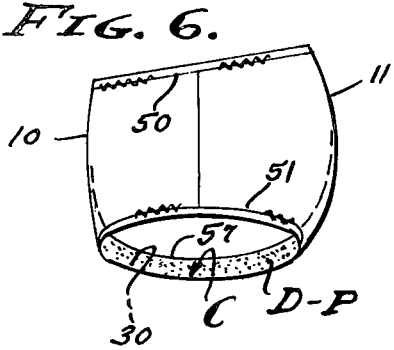
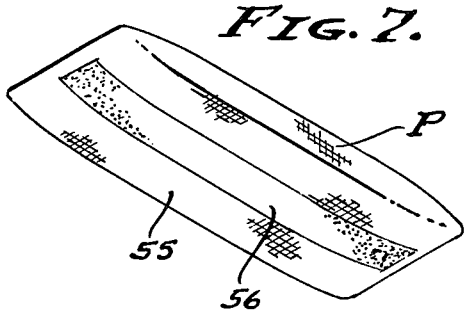
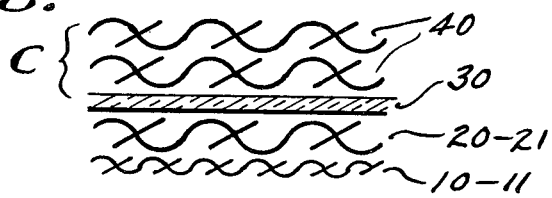

PROTECTIVE PANTY BRIEF

BACKGROUND

Basic undergarments tend to be brief and inconspicuous, and usually made of shear materials reinforced at stress points and/or over vital areas. It is a panty brief with which this invention is concerned, the style and cut of which can vary widely as circumstances require, the general object herein being to provide protection for less fortunate persons who cannot control the discharge of their body liquids, namely urine. Inability to voluntarily stop the flow of urine is quite common and has to do with development of the bladder and associated organs as they are supported by the Paroneal Sling. In short, if the person suffers from incontinence and cannot voluntarily restrict and/or stop the flow of urine, there is the problem of continued seepage resulting in a constant wetting of garments. There are of course various degrees of malfunction in this respect, and various contrivances and absorptive pads have been worn for the collection of said liquids, but with great discomfort to the wearer. However, when the subject person is under reasonable control and able to pay attention to his or her hygene requirements from time to time, then it is entirely possible to wear absorptive materials for the collection of said liquid discharge. Such control can be difficult in the female and it is a panty with which this invention is particularly concerned, a panty that has absorptive properties and a capability of comfortably positioning an additional absorptive pad, all as circumstances require.

The basic undergarment is a panty brief made of relatively shear material, preferably a knit construction designed to stretch in one or both planar directions. For example, the exterior panels of the garment are made from a single knit fabric disposed to stretch laterally (side ways) but not longitudinally (long ways). The interior panels or lining are made from a double knit fabric disposed to stretch both laterally and longitudinally. These knit materials can be of synthetic or natural fibers or any combination thereof, but especially the liner is of highly absorptive material, principally of cotton or the like. The waist band and leg openings are elastic, and the crotch is reinforced as will be described.

Comfort and inconspicuousness are of great concern, while a capacity to collect the liquid discharge must be adequate as well. For example, thin and flimsy materials are generally inadequate for liquid absorption, while a shear garment is desirable for inconspicuousness. Therefore, localized pads and diapers have been resorted to, but to the great discomfort of the user with the ever present problem of its securement and the requirement of a sanitary belt or like harness. And, without securement such pads usually shift out of position. It is to be understood that the use of a pad or diaper is determined by how rapid the discharge and by time periods between change or replacement requirements thereof. In other words, versatility is a requirement, that the panty be self-sufficient at times and that a pad or diaper be installed at other times. Therefore, it is an object of this invention to provide a panty that is comfortably brief, inconspicuous, and which not only has liquid absorptive properties in its concept but which is also adapted to be supplemented by absorptive pads secured in position thereby.

With this invention, the panty is of usual design but lined with absorptive material shielded throughout the critical area by an impervious membrane. It is said membrane which provides a degree of stiffness and body which assures the placement of a pad or diaper, and which restricts the stretch of the panty over that critical area occupied by said pad or diaper. Pads can be secured in place by pressure adhesive strips and are not torn loose by the otherwise continuous stretching and contracting movements, while the more bulky diapers are simply manipulated to shape and positioned and are not dislodged, since the crotch area of this panty is reinforced so as to maintain its area of configuration without distortion that would dislodge the diaper when in use. Furthermore, athletic activities are not restricted when wearing this panty with or without a pad or diaper, as the critical crotch area is reinforced so as to prevent the said otherwise detrimental stretching and working movements.

SUMMARY OF INVENTION

The undergarment of the present invention is a protective panty brief to be worn by a person not in complete control of liquid elimination. Therefore, this garment has the appearance of a shear panty but the construction of a protective panty with liquid absorptive properties. Accordingly, the exterior panels thereof are shear and decorative affording the usual protection to outer garments; and the interior panels thereof are of substantial body affording the absorptive properties required for collecting and containing discharged liquid, namely urine. However, versatility is to be desired and the provision is therefore made to securably maintain the installed position of an absorbent pad or sanitary napkin or diaper, as may be required. Therefore, a feature of this invention is the reinforced crotch area and its double absorptive lining bordered by front and back panel areas of single absorptive lining. Accordingly, the basic panty affords the double absorptive capacity of the crotch backed up by the single absorptive capacity of the embracing front and back panels. When an additional pad or diaper of great absorptive capacity is used, then there is a three fold protection as liquid saturation takes place, and all of which is confined to and within the lining, the exterior panels of the panty being reserved to intervene between said lining and the outer garments that are to be protected against excessive wetness and/or dampness as the case may be.

DRAWINGS

The various objects and features of this invention will be fully understood from the following detailed description of the typical preferred form and application thereof, throughout which description reference is made to the accompanying drawings, in which:

FIG. 1 is a front elevation of the panty.

FIGS. 2 and 3 are flat pattern views of the stretch resistant crotch members, separated in FIG. 2 and sewn together in FIG. 3.

FIGS. 4 and 5 are flat pattern views of the outer panels and lining, FIG. 4 showing the cut form thereof joined by a crotch seam, and FIG. 5 showing the stretch resistant crotch of FIG. 3 sewn thereto.

FIG. 6 is a side view of the panty with the absorbent pad installed therein.

FIG. 7 is a view of the absorbent pad and adhesive strip for its securement, and FIG. 8 is an enlarged fragmentary section taken through the reinforcing crotch of the panty.

PREFERRED EMBODIMENT

Referring now to the drawings, the panty brief is a stretchable undergarment that involves front and back outer panels 10 and 11 of decorative shear fabric, lined with front and back inner panels 20 and 21 of soft absorptive fabric. The panty shown herein is designed for commercial production and therefor displays simplicity and straight forward practicality, for example employing a transverse seam 12 through the crotch in order to use a minimum of material in the flat pattern cutting. Accordingly, the inner and outer panels are cut of separate front and back sections joined at the crotch by a transverse overlock stitch 12 to provide a finished edge, as shown. The crotch is of limited transverse extent with semi-circular concaved leg openings 13 of the outer panels coinciding with semi-circular concaved leg openings 23 of the inner panels. The lateral stretch of the outer panels extends transversely between front and back side edges 15 and 16 of the outer panels coinciding with front and back side edges 25 and 26 of the inner panels. The non-stretch extent of the outer panels extends longitudinally between the front and back waist edges 17 and 18 thereof, coinciding with front and back waist edges 27 and 28 of the inner panel. The coinciding flat pattern of outer fabric and inner lining fabric is shown in FIGS. 4 and 5.

In accordance with this invention the absorptive and reinforcing crotch C is provided as shown in FIG. 3 and comprised of one or more layers of soft absorptive cotton fabric lining 40 in combination with a stretch resistant membrane 30 of flexible supple material. In practice, an imperforate plastic membrane of 0.005 inch polyurethane is employed and disposed between the crotch area of the aforementioned front and back panels of the inner liner 20 and 21 and coextensively underlying the crotch lining 40. Since liquid absorption is the purpose herein, several layers of crotch lining 40 are employed to overlie the said membrane 30. In practice, several layers of crotch lining 40 are employed and single layer of crotch reinforcing membrane 30, all simultaneously cut so as to be coextensive one with the other, with leg portions 31 and 41 of semi-circular form coinciding with the configuration of the aforementioned openings 13 and 23. The said leg openings 31 of member 30 are joined by front and back edges 33 and 34, while the said leg openings 41 and 42 of lining 40 are joined by front and back edges 43 and 44. The said front and back edges are of convexly arcuate form to extend the crotch both anteriorly and posteriorly so as to adequately cover the urinary canal and attendant genitals. The anterior extension of the crotch membrane 30 and overlying crotch lining 40 occupies ⅖ of the longitudinal dimension from seam 12 to the front waist edge 27; while the posterior extension of the crotch membrane 30 and overlying crotch lining 40 occupies 3/5 of the longitudinal dimension from seam 12 to the back waist edge 28. Although the absorbent knit cotton of the crotch lining 40 is double stretch, stretch is practically eliminated by the reinforcing member of impervious stretch resistant plastic; when assembled by sewing together as next described.

(1) The reinforcing and protective crotch is prepared as a sub-assembly by joining the lamination thereof together by overlock stitching at both the front and back edges 33-34 and 43-44; leaving the leg openings 41 and 42 unstitched. This assures anchorage of and a nonshiftable relationship between the said impervious membrane 30 and the overlying absorptive lining or linings 40, the former restricting stretching of the latter.

(2) The reinforcing and protective crotch assembly is fastened into the front and back panels 10-20 (11-21) to overlie the inner lining thereof, by a zig-zag stitching that embraces the aforesaid overlock stitching and applied coextensively along edges 33-34 and 43-44; again leaving the leg openings 31 and 41 unstitched.

(3) The flat pattern assembly is then overlock stitched at the leg openings 13-23 and separately at the front and back waist edges 15-25 and 16-26; leaving the side edges 17-27 and 18-28 unstitched.

(4) The side edges 17-27 and 18-28 of the front and back panels 10 and 11 (20 and 21) are then brought together and overlock stitched, followed by continuing said overlock stitching around the leg openings 13-23 and joining the crotch leg openings 31-41 thereto.

(5) The garment is then completed by applying elastic binding 50 and 51 to the waist and leg openings respectively, secured by zig-zag stitching which embraces the aforementioned overlock stitching, both stitchings providing for stretch of the fabric and said elastic bindings.

From the foregoing it will be seen that the panty brief is laterally stretchable by virtue of the single knit nylon jersey which preferably comprises the front and back outer panels. Although the front and back lining panels are double knit, they are restricted against longitudinal stretching by the outer panels. In accordance with this invention, the crotch assembly adds the double absorptive layers of lining, preferably cotton knit fabric woven with an elastic thread, and all of which is reinforced throughout the crotch area by means of the impervious stretch resistant membrane. When this panty brief is worn as such (without the use of an absorptive pad) there is the confinement of moisture to the extent that it is absorbed by the crotch lining and confined thereto by the said membrane cooperating therewith. When this panty brief is worn with an absorptive pad or sanitary napkin or diaper, it is then that the stretch resistant properties of the protective membrane come into play. The diaper D is a pad that is opened up and fashioned to fit the crotch and held in place by the panty crotch area. Distortion of this crotch area is reduced by the stretch resistant membrane 30 so as to eliminate working of the diaper out of position. The pad or napkin P is an elongated widened body of absorbent material tapered at opposite ends, and for example, with its outer face 55 provided with pressure adhesive stripping 56 extending coextensively with the longitudinal extent thereof, and with its inner face 57 in conformity with the subject persons body parts and overlying the urinary canal. Shear forces that would work against a pad or napkin or a diaper are eliminated by means of the stretch resistant membrane 30 which prevents any substantial augmentation in the area configuration of the crotch C. Accordingly, the extended edges of the pad or napkin or diaper D are frictionally engaged and held tightly in contiguous interengagement between the constricting double knit body panels and the contours of the wearers body. As a result, the external tapered edges as they are shown in FIG. 6 flex to the ever changing contours of the wearers body without displacement therefrom.

Having described only a typical preferred form and application of my invention, I do not wish to be limited or restricted to the specific details herein set forth, but wish to reserve to myself any modifications or variations that may appear to those skilled in the art as set forth within the limits of the following claims:

I claim:

1. A protective undergarment in the form of a panty to be worn by those persons who suffer from incontinence and do not have complete bladder control and the like, and comprised of coextensively stretchable body panels of single knit material to prevent clinging with outer garments and with a crotch area covering the urinary canal and attendant genitals, a full lining of stretchable liquid absorbent double knit material over the stretchable body panels, and a protective shield including an imperforate membrane impervious to said liquid urine and made of stretch resistant material coextensive of said crotch area over which an absorbent pad is removably lodged with its extremities extended contiguously between the stretchable lining over the body panels and wearers body, whereby said absorbent pad is positioned by the crotch area and held secure by constriction of the stretchable lining and body panels frictionally engaged therewith.

2. The protective undergarment as set forth in claim 1, wherein the body panels are of single knit laterally stretchable material to prevent clinging with outer garments and are fully lined with a laterally and longitudinally stretchable liquid absorbent double knit material frictionally engageable with the said extremities of the said absorbent pad held secure thereby.

3. The protective undergarment as set forth in claim 1, wherein the said body panels of single knit material are nylon to prevent clinging with outer garments, and the full lining of stretchable liquid absorbent double knit is predominately of cotton frictionally engageable with the said extremities of the said absorbent pad held secure thereby.

4. The protective undergarment as set forth in claim 1, wherein the said body panels of single knit material are laterally stretchable nylon to prevent clinging with outer garments, and the full lining of liquid absorbent double knit material is laterally and longitudinally stretchable and is predominately of cotton frictionally engageable with the said extremities of the said absorbent pad held secure thereby.

* * * * *